(12) United States Patent
Heaton

(10) Patent No.: US 12,722,871 B1
(45) Date of Patent: Sep. 1, 2026

(54) MEDICATION PEN DISPENSER DEVICE

(71) Applicant: Elijah Keith Heaton, Concord, NC (US)

(72) Inventor: Elijah Keith Heaton, Concord, NC (US)

( * ) Notice: Subject to any disclaimer, the term of this patent is extended or adjusted under 35 U.S.C. 154(b) by 0 days.

(21) Appl. No.: 19/465,132

(22) Filed: Jan. 30, 2026

(51) Int. Cl.
*B65D 83/02* (2006.01)
*A61M 5/00* (2006.01)

(52) U.S. Cl.
CPC ............. *B65D 83/02* (2013.01); *A61M 5/002* (2013.01)

(58) Field of Classification Search
CPC ........ B65D 83/02; B65D 83/00; B65D 85/07; B65D 85/08; B65D 85/10; B65D 85/1009; B65D 85/20; B65D 85/24; B65D 85/28; A61M 5/002
USPC .......................................................... 206/366
See application file for complete search history.

(56) References Cited

U.S. PATENT DOCUMENTS 3,439,797 A * 4/1969 Cooper .............. B65D 85/1009 206/267
6,406,107 B1 * 6/2002 Franczak .................. A47F 1/08 211/49.1
D1,041,942 S * 9/2024 Shoaf ............................. D6/515
2020/0178705 A1 * 6/2020 Barzee ................. A47B 57/585
2021/0092997 A1 * 4/2021 Lin ......................... A24F 15/06
2022/0277257 A1 * 9/2022 Ferreira .................... A47F 1/08

* cited by examiner

*Primary Examiner* — Javier A Pagan
(74) *Attorney, Agent, or Firm* — PATENTFILE, LLC; Bradley C. Fach; Steven R. Kick

(57) ABSTRACT

A medication pen dispenser device may include a mount that may be removably coupled to a dispenser. The mount may include a body having one or more mount walls. A mount wall may have a mounting aperture and a mounting surface configured to be coupled to an object that the device is desired to be coupled to. The mounting surface and the mounting aperture may be positioned on opposite sides of the mount wall. The dispenser may include a plurality of walls with a storage cavity formed between the walls. A dispensing aperture may be in communication with the storage cavity. A mounting arm may be coupled to a wall of the dispenser. The mount and the dispenser may be removably coupled together by inserting the mounting arm into the mounting aperture. The storage cavity may be sized to hold a plurality of medication pens or other elongated medication containers.

20 Claims, 7 Drawing Sheets

MEDICATION PEN DISPENSER DEVICE

FIELD OF THE INVENTION

This patent specification relates to the field of devices for storing and dispensing medication containers. More specifically, this patent specification relates to a device for storing and dispensing medication containers, such as which may be used to store and dispense injectable medication pens in a cold storage device so that the medication pens may be dispensed in date order of oldest first while maximizing storage space within the cold storage device.

BACKGROUND

Medication pen containers such as prefilled insulin pens are commonly stored loosely on refrigerator shelves, in drawers, or in door compartments, which offers little control over storage order or use-by sequence and can contribute to wasted medication and disorganized space. Patients and caregivers typically store unopened medication pens on flat refrigerator shelves, in crisper drawers, or in door shelves or "butter" compartments alongside food items. These locations are chosen for convenience and available space rather than for any systematic arrangement of pens according to fill date, expiration date, or recommended use period, and they are often unmonitored with respect to medication inventory and organization Storing pens loosely on shelves, in drawers, or in door compartments makes it difficult to visually distinguish which pen should be used next, particularly when multiple lots or prescription refills are present, increasing the likelihood that newer pens are used before older ones, or that older pens remain at the back and ultimately expire. This disorganized storage can also make it harder for a user to quickly assess remaining supply, can require repeated handling and searching for the correct pen, exposes the pens to potential physical damage and/or accidental discharge of the medication, and may expose pens to suboptimal temperature regions such as very cold back-wall areas or warmer door zones within the refrigerator.

Mounting and organizing these pens on the refrigerator wall in a defined, date-based dispensing order addresses both sequencing and space-utilization problems that existing storage practices and simple pen holders do not solve Therefore, a need exists for novel devices which are configured for mounting and organizing these pens on the refrigerator wall in a defined, date-based dispensing order that addresses both sequencing and space-utilization problems that existing storage practices and simple pen holders do not solve.

BRIEF SUMMARY OF THE INVENTION

A medication pen dispenser device is provided which may be configured to store and dispense medication pens or other elongated medication containers. Preferably, the device may be configured for mounting and organizing medication pens or other elongated medication containers on a vertical refrigerator wall in a defined, date-based dispensing order.

In some embodiments, the device may include a mount that may be removably coupled to a dispenser. The mount may include a body, and one or more mount walls may be formed by the body. A mount wall may have a mounting surface and a mounting aperture. The mounting surface and the mounting aperture may be positioned on opposite sides of the mount wall. The mounting surface may be coupled to an object that the device is desired to be coupled to. The dispenser may include a first major wall, a second major wall, a bottom wall, a first minor wall, and a second minor wall. The first minor wall may be coupled to the first major wall and the second major wall. The second minor wall may be coupled to the first major wall and the second major wall. The first major wall may be substantially parallel to the second major wall, and the first minor wall may be substantially parallel to the second minor wall. The bottom wall may be coupled to the first major wall and the second major wall, and the bottom wall may be substantially perpendicular to the first minor wall and to the second minor wall. A storage cavity may be formed between the first major wall, the second major wall, the bottom wall, the first minor wall, and the second minor wall. A dispensing aperture may be in communication with the storage cavity, and the dispensing aperture may separate the first minor wall from the bottom wall. A mounting arm may be coupled to the first major wall so that the storage cavity and the mounting arm are positioned on opposite sides of the first major wall. The mount and the dispenser may be configured to be removably coupled together by inserting the mounting arm into the mounting aperture. The storage cavity may be sized to hold a plurality of medication pens or other elongated medication containers, and the dispensing aperture may preferably be sized to allow a single medication pen or other elongated medication container to be removed from the storage cavity at one time.

In further embodiments, the device may have a mounting arm that includes a horizontal projection and a vertical projection. Preferably, the horizontal projection may be substantially parallel to the first major wall, and the vertical projection may separate the horizontal projection from the first major wall so that an arm channel is formed between the horizontal projection and the first major wall. Preferably, the mount may include a support wall in contact with the mounting aperture, and the support wall may be positioned in the arm channel when the mount and the dispenser are removably coupled together Numerous objects, features and advantages of the present invention will be readily apparent to those of ordinary skill in the art. Some example objects of the present invention are listed below.

One object of the present invention is to provide a medication pen dispenser device that may be used to organize medication pens so that they are dispensed in date order of oldest first.

Another object is to provide a medication pen dispenser device that may be used to organize medication pens so that the device stores the pens up on the refrigerator wall saving valuable shelf or drawer space.

Another object is to provide a medication pen dispenser device that is easily removed from the refrigerator for refilling and which may have a storage cavity that may be configured in at least two widths (0.600 and 0.800 inches inside width) to accommodate the majority of different size pens available.

BRIEF DESCRIPTION OF THE DRAWINGS

Some embodiments of the present invention are illustrated as an example and are not limited by the figures of the accompanying drawings, in which like references may indicate similar elements and in which.

DETAILED DESCRIPTION OF THE INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

Figure 1:
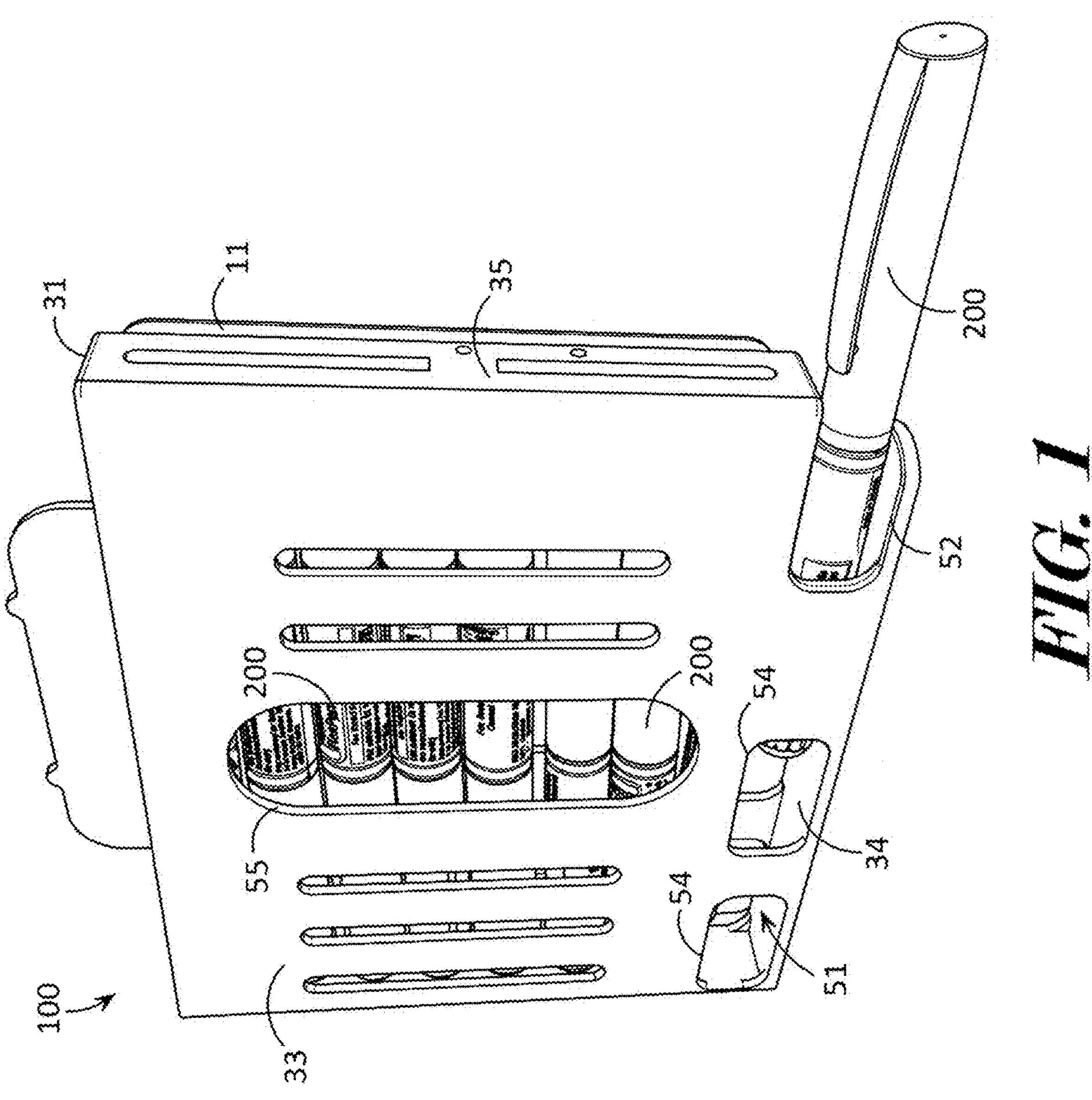
FIG. 1 depicts a perspective view of an example of a medication pen dispenser device dispensing a single medication pen according to various embodiments described herein.

For purposes of description herein, the terms "upper," "lower," "left," "right," "rear," "front," "side," "vertical," "horizontal," and derivatives thereof shall relate to the invention as oriented in FIG. 1. However, one will understand that the invention may assume various alternative orientations and step sequences, except where expressly specified to the contrary. Therefore, the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Although the terms "first," "second," etc. are used herein to describe various elements, these elements should not be limited by these terms. These terms are only used to distinguish one element from another element. For example, the first element may be designated as the second element, and the second element may be likewise designated as the first element without departing from the scope of the invention.

As used in this application, the term "about" or "approximately" refers to a range of values within plus or minus 20% of the specified number. Additionally, as used in this application, the term "substantially" means that the actual value is within about 10% of the actual desired value, more preferably within about 5% of the actual desired value and even more preferably within about 1% of the actual desired value of any variable, element or limit set forth herein.

A new medication pen dispenser device is discussed herein. In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention and is not intended to limit the invention to the specific embodiments illustrated by the figures or description below.

Figure 6:
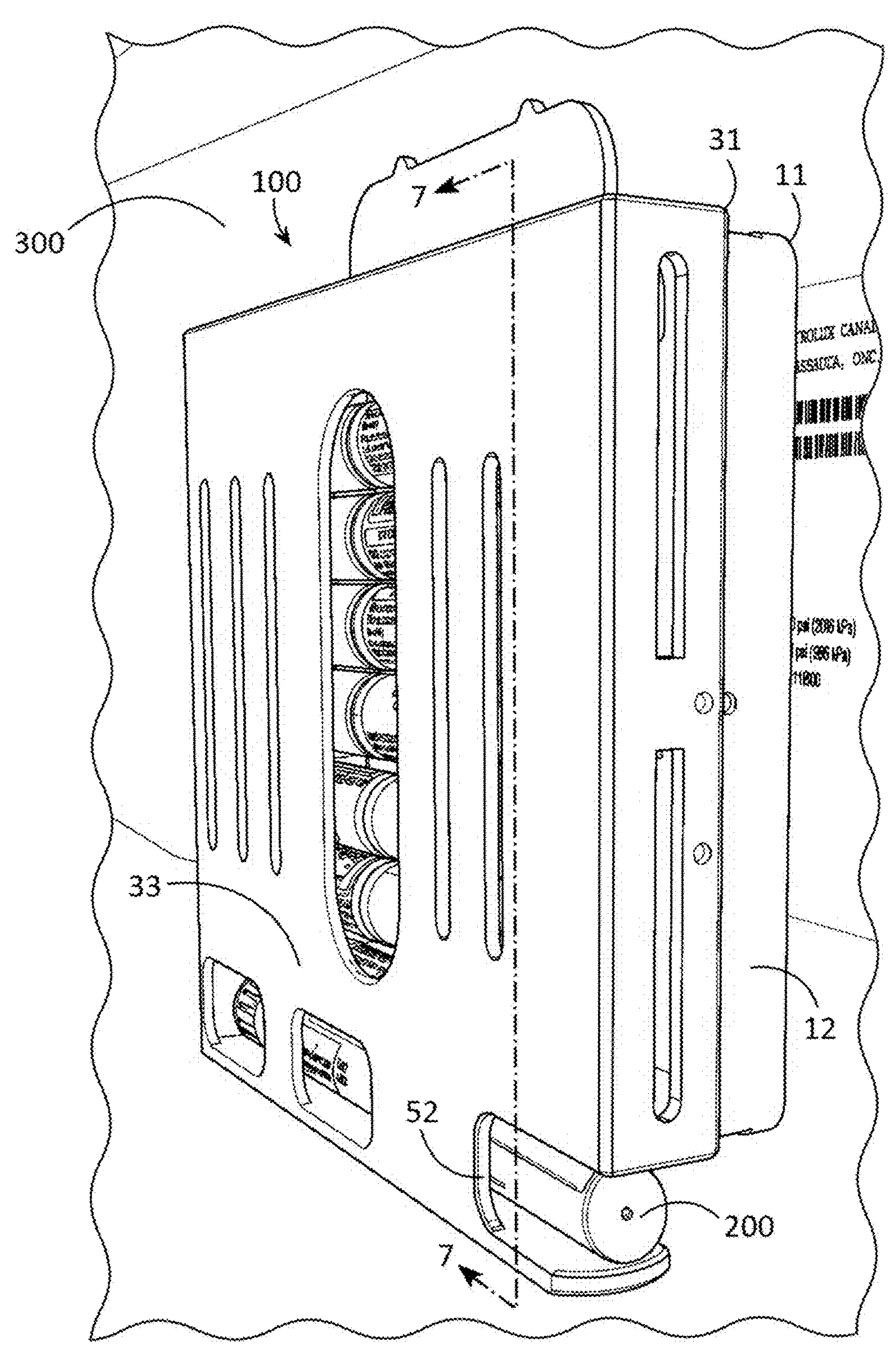
FIG. 6 shows a side perspective view of an example medication pen dispenser device coupled to an interior wall of a refrigerator according to various embodiments described herein.
Figure 7:
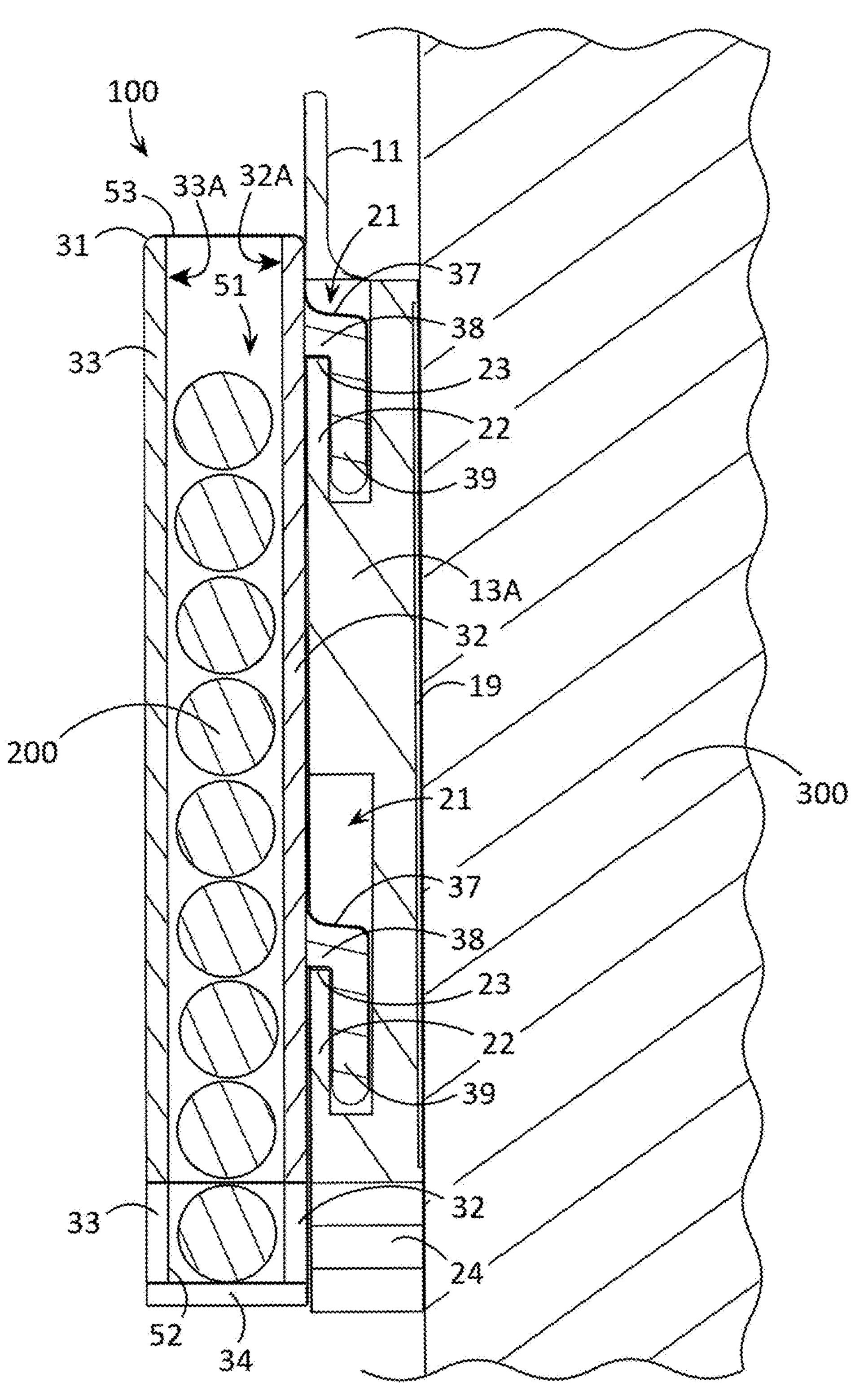
FIG. 7 depicts a sectional, through line 7-7 shown in FIG. 6, elevation view of an example medication pen dispenser device coupled to an interior wall of a refrigerator according to various embodiments described herein.

The present invention will now be described by example and through referencing the appended figures representing preferred and alternative embodiments. FIGS. 1, 6, and 7 illustrate an example of a medication pen dispenser device ("the device") 100 according to various embodiments. In some embodiments, the device 100 may comprise a mount 11 that may be removably coupled to a dispenser 31. The mount 11 may include a body 12, and one or more mount walls 13A, 13B, 13C, may be formed by the body 12. A mount wall 13A, 13B, 13C, may comprise a mounting surface 14 and a mounting aperture 15A, 15B. The mounting surface 14 and the mounting aperture 15A, 15B, may be positioned on opposite sides of the mount wall 13A, 13B, 13C. The mounting surface 14 may be coupled to an object that the device 100 is desired to be coupled to. The dispenser 31 may comprise a first major wall 32, a second major wall 33, a bottom wall 34, a first minor wall 35, and a second minor wall 36. The first minor wall 35 may be coupled to the first major wall 32 and the second major wall 33. The second minor wall 36 may be coupled to the first major wall 32 and the second major wall 33. The first major wall 32 may be substantially parallel to the second major wall 33, and the first minor wall 35 may be substantially parallel to the second minor wall 36. The bottom wall 34 may be coupled to the first major wall 32 and the second major wall 33, and the bottom wall 34 may be substantially perpendicular to the first minor wall 35 and to the second minor wall 36. A storage cavity 51 may be formed between the first major wall 32, the second major wall 33, the bottom wall 34, the first minor wall 35, and the second minor wall 36. A dispensing aperture 52 may be in communication with the storage cavity 51, and the dispensing aperture 52 may separate the first minor wall 35 from the bottom wall 34. A mounting arm 37 may be coupled to the first major wall 32 so that the storage cavity 51 and the mounting arm 37 are positioned on opposite sides of the first major wall 32. The mount 11 and the dispenser 31 may be configured to be removably coupled together by inserting the mounting arm 37 into the mounting aperture 15A, 15B. The storage cavity 51 may be sized to hold a plurality of medication pens or other elongated medication containers, and the dispensing aperture 52 may be sized to allow a single medication pen or other elongated medication container to be removed from the storage cavity 51 at one time.

Figure 2:
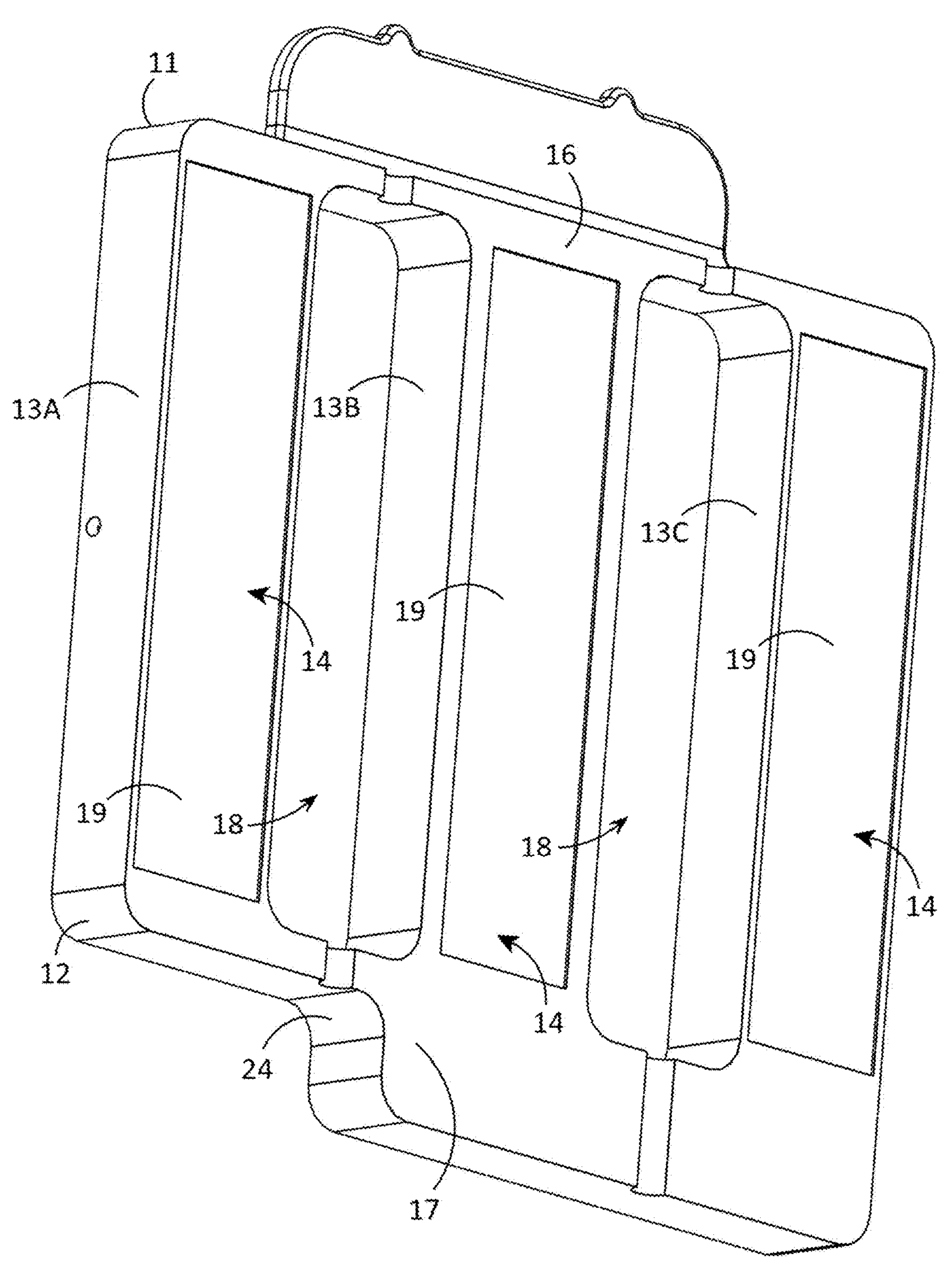
FIG. 2 illustrates a first side perspective view of an example of a mount according to various embodiments described herein.
Figure 3:
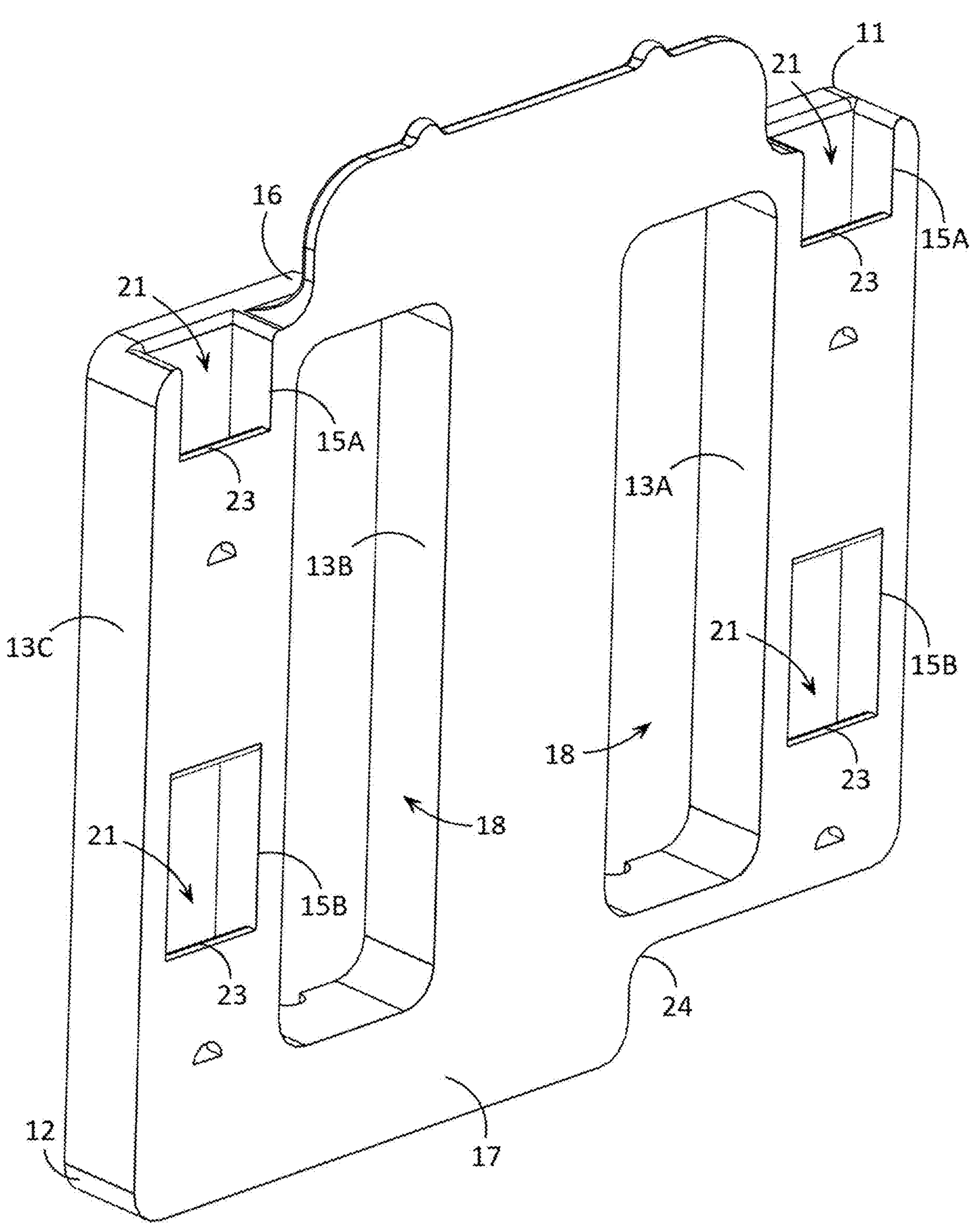
FIG. 3 shows a second side perspective view of an example of a mount according to various embodiments described herein.
Figure 4:
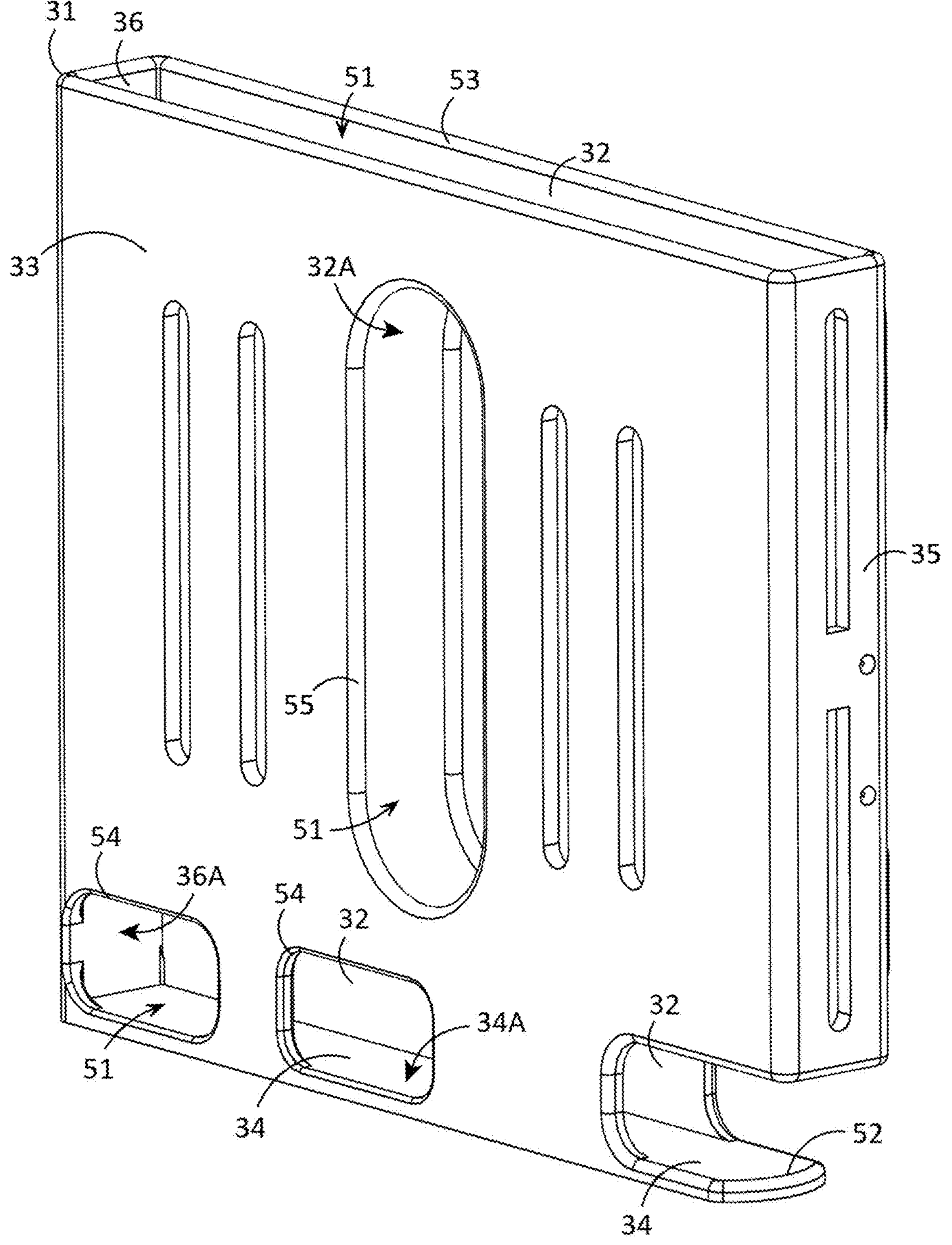
FIG. 4 depicts a first side perspective view of an example of a dispenser according to various embodiments described herein.
Figure 5:
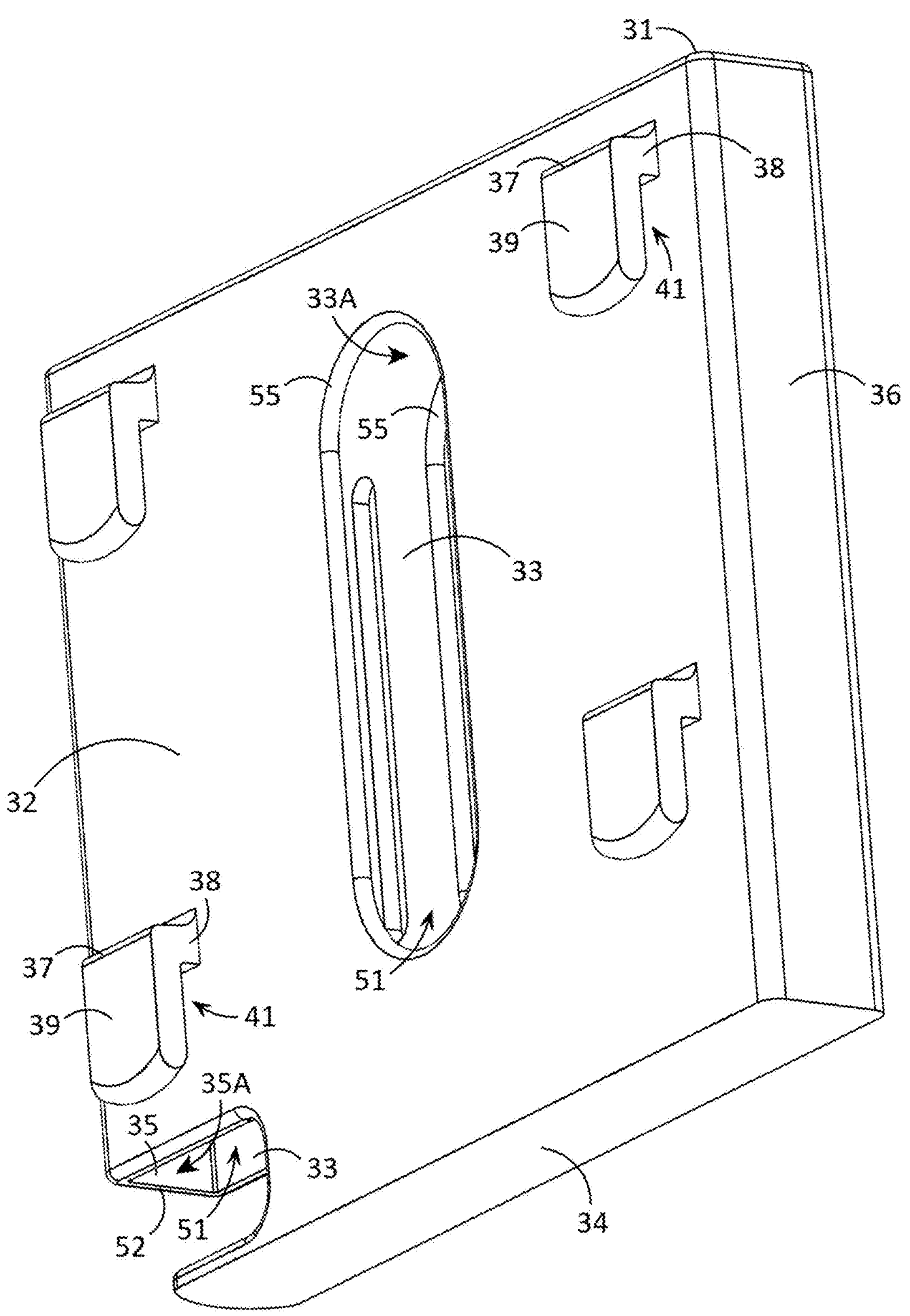
FIG. 5 illustrates a second side perspective view of an example of a dispenser according to various embodiments described herein.

The device 100 may include a mount 11 that may be configured to be coupled to an object that the device 100 is desired to be coupled to, such as an interior wall of a refrigerator 300 or other cold storage device. Preferably, the mount 11 may be made from or may comprise a substantially rigid plastic or other structurally rigid material. The mount 11 may include a body 12 which may be configured in any size and shape. In preferred embodiments, one or more mount walls 13A, 13B, 13C, may be formed by the body 12 such that the mount 11 may comprise one or more mount walls 13A, 13B, 13C. Mount walls 13A, 13B, 13C, may be configured in any size and shape. Preferably, a mount wall 13A, 13B, 13C, may comprise a generally rectangular prism shape, as perhaps best shown in FIGS. 2 and 3. In some embodiments, the body 12 may comprise three mount walls 13A, 13B, 13C, that may be coupled together via lateral extensions 16, 17. Optionally, the body 12 may comprise one or more body voids 18 which may comprise openings, cavities, etc., such as which may be used to decrease the amount of material needed to make the body 12.

In some embodiments, one or more mount walls 13A, 13B, 13C, may comprise a mounting surface 14. A mounting surface 14 may be configured in any size and shape. Preferably, a mounting surface 14 may comprise a general flat or planar surface, such as which may be used to contact or be coupled to a flat or planar surface, such as an interior vertical wall of a refrigerator 300. In preferred embodiments, one or more, such as each, mounting surface 14 of the body 12 of the mount 11 may be coupled to an object that the device 100 is desired to be coupled to. Optionally, one or more of the mounting surfaces 14 may comprise an adhesive 19 which may be used to adhesively couple the mount 11 to an object that the device 100 is desired to be coupled to. For example, an adhesive 19 may comprise a double-sided adhesive tape, such as Scotch™ Brand Extreme Mounting Tape that is rated for underwater and cold weather as manufactured by 3M having a headquarters in Maplewood, Minnesota. Further example adhesives 19 may include but are not limited to natural adhesives including natural resins, bioadhesives, or synthetic adhesives such as epoxy, polyurethane, acrylate, including methacrylates and epoxy diacrylates (which are also known as vinyl resins), cyanoacrylate and acrylic polymer based adhesives The mount 11 may comprise one or more mounting apertures 15A, 15B, that may be formed into the one or more mount walls 13A, 13B, 13C, so that the mounting surface(s) 14 and mounting aperture(s) 15A, 15B, of a mount wall, and more preferably each mounting wall, are positioned on opposite sides of the mount wall(s). In some embodiments, one or more mount walls 13A, 13B, 13C, may comprise one or more mounting apertures 15A, 15B. For example, a mount wall 13A, 13B, 13C, may comprise an upper mounting aperture 15A and a lower mounting aperture 15B. The mounting surface(s) 14 and the mounting aperture(s) 15A, 15B, may be positioned on opposite sides of the body 12, such as on opposite sides of a mount wall 13A, 13B, 13C. Each mounting aperture 15A, 15B, may be in communication with an arm cavity 21. An arm cavity 21 may comprise a recess within a mount wall 13A, 13B, 13C, which may be sized and shaped to receive all or portions of a mounting arm 37 so that all or portion of the mounting arm 37 may fit within the mount wall 13A, 13B, 13C. Generally, a mounting aperture 15A, 15B, may be an opening in the mount wall 13A, 13B, 13C, that allows a mounting arm 37 to enter an arm cavity 21, and the arm cavity 21 preferably may be larger than the mounting aperture 15A, 15B, that the arm cavity 21 is in communication with. Preferably, the mount 11 may comprise a support wall 22 that may make the opening of a mounting aperture 15A, 15B, smaller than the arm cavity 21 that the mounting aperture 15A, 15B, is in communication with. The support wall 22 may comprise an upper lip 23 that may form a portion of the mounting aperture 15A, 15B, (e.g., the support wall 22 may be in contact with the mounting aperture 15A, 15B,). The arm cavity 21 may extend below the upper lip 23 of the support wall 22 that the arm cavity 21 is in contact with. The support wall 22 may comprise a structure of any shape and size that is configured to fit between the vertical projection 39 of a mounting arm 37 and the first major wall 32. Optionally, a support wall 22 may comprise a plate shape having a relatively thinner dimension than the surrounding portions of the mount wall 13A, 13B, 13C, that the support wall 22 is formed in.

The device 100 may comprise a dispenser 31 that may be coupled, and more preferably removably coupled, to the mount. A dispenser 31 and mount 11 that are removably coupled together may be repeatedly coupled and uncoupled from each other without damage. Generally, a dispenser 31 may comprise a container configured to hold or contain one or more medication pens 200 or other elongated medication containers. The dispenser 31 may comprise a storage cavity 51 that may enable the dispenser 31 to receive and store a plurality of medication pens 200 or other elongated medication containers. A user may retrieve a medication pen 200 from the dispenser 31 by withdrawing the medication pen 200 from a dispensing aperture 52.

Preferably, the dispenser 31 may be made from or may comprise a substantially rigid plastic or other structurally rigid material. The dispenser 31 may be configured in any size and shape. In preferred embodiments, the dispenser 31 may comprise a first major wall 32, a second major wall 33, a bottom wall 34, a first minor wall 35, and a second minor wall 36. Generally, the major walls 32, 33, may be larger than the minor walls 35, 36. The walls 32, 33, 34, 35, 36, may form and bound the storage cavity 51 so that the storage cavity 51 may be formed between the first major wall 32, the second major wall 33, the bottom wall 34, the first minor wall 35, and the second minor wall 36.

In preferred embodiments, the first minor wall 35 may be coupled to the first major wall 32 and the second major wall 33, and the second minor wall 36 may be coupled to the first major wall 32 and the second major wall 33. The first major wall 32 may be substantially parallel (such as plus or minus 5 degrees of parallel) to the second major wall 33, and the first minor wall 35 may be substantially parallel (such as plus or minus 5 degrees of parallel) to the second minor wall 36. The bottom wall 34 may be coupled to the first major wall 32 and the second major wall 33, and the bottom wall 34 may be substantially perpendicular to the first major wall 32, the second major wall 33, the first minor wall 35, and the second minor wall 36.

The walls 32, 33, 34, 35, 36, may be configured in any size and shape. Preferably, the walls may comprise a generally planar rectangular prism shape having a thickness that is the smallest dimension. The first major wall 32 may comprise a first major wall interior surface 32A, the second major wall 33 may comprise a second major wall interior surface 33A, the bottom wall 34 may comprise a bottom wall interior surface 34A, the first minor wall 35 may comprise a first minor wall interior surface 35A, and the second minor wall 36 may comprise a second minor wall interior surface 36A.

In preferred embodiments, the interior surfaces 32A, 33A, 34A, 35A, 36A, of the walls 32, 33, 34, 35, 36, that form the storage cavity 51 may be flat or planar in shape so that the storage cavity 51 may be generally rectangular prism in shape. The storage cavity 51 may be sized and shaped to store a plurality of medication pens 200 in a stacked orientation. Optionally, the storage cavity 51 may be configured in one or more widths (distance the interior surfaces 32A, 33A, of the major walls 32, 33, are separated from each other) to accommodate the majority of different size pens available. For example, the storage cavity 51 may be configured in a width (distance between the first major wall interior surface 32A and the second major wall interior surface 33A) of approximately 0.600 inches (plus or minus 0.100 inches) to accommodate relatively narrower medication pens 200. As another example, the storage cavity 51 may be configured in a width of approximately 0.800 inches (plus or minus 0.100 inches) to accommodate relatively wider medication pens 200. In yet further embodiments, the storage cavity may be configured in a width ranging from 0.600 inches to 1.30 inches.

In preferred embodiments, the first minor wall interior surface 35A may be coupled to the first major wall interior surface 32A and the second major wall interior surface 33A, and the second minor wall interior surface 36A may be coupled to the first major wall interior surface 32A and the second major wall interior surface 33A. The first major wall interior surface 32A may be substantially parallel (such as plus or minus 5 degrees of parallel) to the second major wall interior surface 33A, and the first minor wall interior surface 35A may be substantially parallel (such as plus or minus 5 degrees of parallel) to the second minor wall interior surface 36A. The bottom wall interior surface 34A may be coupled to the first major wall interior surface 32A and the second major wall interior surface 33A, and the bottom wall interior surface 34A may be substantially perpendicular to the first major wall interior surface 32A, the second major wall interior surface 33A, the first minor wall interior surface 35A, and the second minor wall interior surface 36A.

The dispenser 31 may comprise a dispensing aperture 52 that is in communication with the storage cavity 51. The dispensing aperture 52 may be sized and shaped to allow medication pens 200 or other elongated medication containers in the storage cavity 51 to be withdrawn from the storage cavity 51 proximate to the bottom wall 34. Preferably, the dispensing aperture 52 may be sized and shaped to allow a single medication pen 200 or other elongated medication container in the storage cavity 51 to be withdrawn from the storage cavity 51 at one time.

The dispensing aperture 52 may be configured in any size and shape. Preferably, the dispensing aperture 52 separates the first minor wall 35 from the bottom wall 34. In some embodiments, a portion of the dispensing aperture 52 may be formed in the first major wall 32 and/or a portion of the dispensing aperture 52 may be formed in the second major wall 33. In preferred embodiments, the dispensing aperture 52 may extend into the first major wall 32 and/or into the second major wall 33 a greater distance than the dispensing aperture 52 may extend into the another wall so that the ability of a user to grasp the side(s) of a medication pen 200 or other elongated medication container in the storage cavity 51 may be facilitated when removing the medication pen 200 or other elongated medication container from the storage cavity 51.

The dispenser 31 may comprise a filling aperture 53 which may be sized and shaped to allow medication pens 200 or other elongated medication containers to be deposited into the storage cavity 51. In preferred embodiments, the filling aperture 53 may be formed: into a portion of the first major wall 32 that is distal to the bottom wall 34; into a portion of the second major wall 33 that is distal to the bottom wall 34; into a portion of the first minor wall 35 that is distal to the bottom wall 34; and/or into a portion of the second minor wall 36 that is distal to the bottom wall 34. In further preferred embodiments, the filling aperture 53 may be formed into or disposed on the dispenser 31 so that the bottom wall 34 and filling aperture 53 are opposingly positioned to each other.

In some embodiments, the dispenser 31 may comprise an access aperture 54 that is in communication with the storage cavity 51. The access aperture 54 may be disposed proximate to the bottom wall 34 (such as within 0.5 inches of the bottom wall 34), and the access aperture 54 may be sized and shaped to allow a user to touch or manipulate a portion of a medication pen 200 or other elongated medication container in the storage cavity 51 that is resting on the bottom wall 34 so that the ability of the user to remove the medication pen 200 or other elongated medication container resting on the bottom wall 34 may be enhanced. For example, the user may grasp an end of a medication pen 200 resting on the bottom wall 34 through the dispensing aperture 52 and the user may also press or slide another portion of the medication pen 200 through the access aperture 54. In preferred embodiments, the second major wall 33 of the dispenser 31 may comprise one or more access apertures 54 that are positioned proximate to the bottom wall 34.

In some embodiments, the second major wall 33 of the dispenser 31 may comprise a viewing aperture 55 that is in communication with the storage cavity 51. Preferably, the viewing aperture 55 may be centrally disposed or located on the second major wall 33, such that the viewing aperture 55 may be approximately equidistant between the first minor wall 35 and the second minor wall 36 and/or such that the viewing aperture 55 may be approximately equidistant between the bottom wall 34 and the filling aperture 53. The viewing aperture 55 may be sized and shaped to allow the central portion of medication pens 200 or other elongated medication containers in the storage cavity 51 to be viewed by a user so that the user may observe one or more properties of one or more of the medication pens 200 or other elongated medication containers in the storage cavity 51, such as label color, label wording or medication name, expiration date, etc. In preferred embodiments, the A dispenser 31 may be coupled to the mount 11 via any suitable coupling method which may enable the mount 11 to support the dispenser 31 and any medication pens 200 or other elongated medication containers in the storage cavity 51. In preferred embodiments, the dispenser 31 and mount 11 may be removably coupled together so that the dispenser 31 may be easily detached from and reattached to the mount 11 while the mount 11 remains secured to a support object, such as an interior wall of a refrigerator 300.

In preferred embodiments, the dispenser 31 may comprise one or more mounting arms 37 and the mount 11 may comprise one or more arm cavities 21, and the mount 11 and the dispenser 31 may be configured to be removably coupled together by inserting at least one mounting arm 37 into at least one mounting aperture 15A, 15B. The one or more mounting arms 37 may be coupled to the first major wall 32 so that the storage cavity 51 and the mounting arm(s) 37 are positioned on opposite sides of the first major wall 32. Optionally, a mount 11 may comprise one or more mounting arms 37 and a dispenser 31 may comprise one or more mounting apertures 15A, 15B, and arm cavities 21.

In preferred embodiments, a mounting arm 37 may comprise a horizontal projection 38 and a vertical projection 39. The vertical projection 39 may be coupled to the horizontal projection 38, and the horizontal projection 38 may also be coupled to the first major wall 32. The vertical projection 39 may separate a horizontal projection 38 from a first major wall 32 so that an arm channel 41 is formed between the horizontal projection 38 and the first major wall 32. Preferably, the horizontal projection 38 may be substantially parallel (plus or minus 5 degrees) to the first major wall 32.

To removably couple the mount 11 and dispenser 31 together, the mounting arm 37 may be inserted through a mounting aperture 15A, 15B, so that the vertical projection 39 is positioned in the arm cavity 21 while the horizontal projection 38 of the mounting arm 37 is resting on the upper lip 23. Preferably, the vertical projection 39 may separate the horizontal projection 38 from the first major wall 32 (to form an arm channel 41) a similar distance as the thickness of the support wall 22 in contact with the mounting aperture 15A, 15B, that the horizontal projection 38 is configured to be inserted into so that the support wall 22 may be positioned in and fit snugly in the arm channel 41 formed between the vertical projection 39 and the first major wall 32.

In some embodiments, the mount 11 may comprise a retrieval cutout 24 that may be aligned with and positioned proximate to the dispensing aperture 52 when the mount 11 and the dispenser 31 are removably coupled together as perhaps best shown in FIGS. 6 and 7. A retrieval cutout 24 may comprise a cutout in the mount 11, such as in a lower lateral extension 17, which may enable a user to position one or more fingers in the retrieval cutout 24 in order to facilitate the user's ability the gasp a portion of a medication pen 200 or other elongated medication container resting on the bottom wall 34 in the storage cavity 51.

While some exemplary shapes and sizes have been provided for elements of the device 100, it should be understood to one of ordinary skill in the art that the mount 11, mounting apertures 15A, 15B, dispenser 31, mounting arms 37, and any other element described herein may be configured in a plurality of sizes and shapes including "T" shaped, "X" shaped, square shaped, rectangular shaped, cylinder shaped, cuboid shaped, hexagonal prism shaped, triangular prism shaped, or any other geometric or non-geometric shape, including combinations of shapes. It is not intended herein to mention all the possible alternatives, equivalent forms or ramifications of the invention. It is understood that the terms and proposed shapes used herein are merely descriptive, rather than limiting, and that various changes, such as to size and shape, may be made without departing from the spirit or scope of the invention.

Additionally, while some materials have been provided, in other embodiments, the elements that comprise the device 100 may be made from or may comprise durable materials such as aluminum, steel, other metals and metal alloys, wood, hard rubbers, hard plastics, fiber reinforced plastics, carbon fiber, fiberglass, resins, polymers or any other suitable materials including combinations of materials. Additionally, one or more elements may be made from or may comprise durable and slightly flexible materials such as soft plastics, silicone, soft rubbers, or any other suitable materials including combinations of materials. In some embodiments, one or more of the elements that comprise the device 100 may be coupled or connected together with heat bonding, chemical bonding, adhesives, clasp type fasteners, clip type fasteners, rivet type fasteners, threaded type fasteners, other types of fasteners, or any other suitable joining method. In other embodiments, one or more of the elements that comprise the device 100 may be coupled or removably connected by being press fit or snap fit together, by one or more fasteners such as hook and loop type or Velcro® fasteners, magnetic type fasteners, threaded type fasteners, sealable tongue and groove fasteners, snap fasteners, clip type fasteners, clasp type fasteners, ratchet type fasteners, a push-to-lock type connection method, a turn-to-lock type connection method, a slide-to-lock type connection method or any other suitable temporary connection method as one reasonably skilled in the art could envision to serve the same function. In further embodiments, one or more of the elements that comprise the device 100 may be coupled by being one of connected to and integrally formed with another element of the device 100.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A medication pen dispenser device, the device comprising:

a mount, wherein the mount comprises:

i. a body; and ii. at least one mount wall formed by the body, wherein the at least one mount wall comprises a mounting surface, wherein the at least one mount wall comprises a mounting aperture, and wherein the mounting surface and the mounting aperture are positioned on opposite sides of the at least one mount wall; and a dispenser, wherein the dispenser comprises:

i. a first major wall, a second major wall, a bottom wall, a first minor wall, and a second minor wall, wherein the first minor wall is coupled to the first major wall and the second major wall; wherein the second minor wall is coupled to the first major wall and the second major wall, wherein the first major wall is substantially parallel to the second major wall, wherein the first minor wall is substantially parallel to the second minor wall, wherein the bottom wall is coupled to the first major wall and the second major wall, and wherein the bottom wall is substantially perpendicular to the first minor wall and to the second minor wall;

ii. a storage cavity formed between the first major wall, the second major wall, the bottom wall, the first minor wall, and the second minor wall;

iii. a dispensing aperture that is in communication with the storage cavity, wherein the dispensing aperture separates the first minor wall from the bottom wall; and iv. a mounting arm coupled to the first major wall so that the storage cavity and the mounting arm are positioned on opposite sides of the first major wall, wherein the mount and the dispenser are configured to be removably coupled together by inserting the mounting arm into the mounting aperture.

2. The device of claim 1, wherein a portion of the dispensing aperture is formed in the first major wall.

3. The device of claim 1, wherein a portion of the dispensing aperture is formed in the second major wall.

4. The device of claim 1, further comprising a filling aperture, wherein the filling aperture is disposed on the dispenser so that the bottom wall and filling aperture are opposingly positioned to each other.

5. The device of claim 1, wherein the mounting arm comprises a horizontal projection and a vertical projection.

6. The device of claim 5, wherein the horizontal projection is substantially parallel to the first major wall.

7. The device of claim 5, wherein the vertical projection separates the horizontal projection from the first major wall so that an arm channel is formed between the horizontal projection and the first major wall.

8. The device of claim 7, wherein the mount comprises a support wall in contact with the mounting aperture, and wherein the support wall is positioned in the arm channel when the mount and the dispenser are removably coupled together.

9. The device of claim 1, wherein the mounting surface comprises an adhesive.

10. The device of claim 1, wherein the mount comprises a retrieval cutout, and wherein the retrieval cutout is aligned with and positioned proximate to the dispensing aperture when the mount and the dispenser are removably coupled together.

11. The device of claim 1, wherein the second major wall comprises an access aperture that is positioned proximate to the bottom wall.

12. The device of claim 1, wherein the second major wall comprises a viewing aperture, wherein the viewing aperture is located centrally on the second major wall.

13. A medication pen dispenser device, the device comprising:

a mount, wherein the mount comprises:

i. a body; and ii. at least one mount wall formed by the body, wherein the at least one mount wall comprises a mounting surface, wherein the at least one mount wall comprises a mounting aperture, and wherein the mounting surface and the mounting aperture are positioned on opposite sides of the at least one mount wall; and a dispenser, wherein the dispenser comprises:

i. a first major wall, a second major wall, a bottom wall, a first minor wall, and a second minor wall, wherein the first minor wall is coupled to the first major wall and the second major wall; wherein the second minor wall is coupled to the first major wall and the second major wall, wherein the first major wall is substantially parallel to the second major wall, wherein the first minor wall is substantially parallel to the second minor wall, wherein the bottom wall is coupled to the first major wall and the second major wall, and wherein the bottom wall is substantially perpendicular to the first minor wall and to the second minor wall;

ii. a storage cavity formed between the first major wall, the second major wall, the bottom wall, the first minor wall, and the second minor wall;

iii. a dispensing aperture that is in communication with the storage cavity, wherein the dispensing aperture separates the first minor wall from the bottom wall; and iv. a mounting arm coupled to the first major wall so that the storage cavity and the mounting arm are positioned on opposite sides of the first major wall, wherein the mount and the dispenser are configured to be removably coupled together by inserting the mounting arm into the mounting aperture, wherein the mounting arm comprises a horizontal projection and a vertical projection, wherein the horizontal projection is substantially parallel to the first major wall, wherein the vertical projection separates the horizontal projection from the first major wall so that an arm channel is formed between the horizontal projection and the first major wall, wherein the mount comprises a support wall in contact with the mounting aperture, and wherein the support wall is positioned in the arm channel when the mount and the dispenser are removably coupled together.

14. The device of claim 13, wherein a portion of the dispensing aperture is formed in the first major wall.

15. The device of claim 13, wherein a portion of the dispensing aperture is formed in the second major wall.

16. The device of claim 13, further comprising a filling aperture, wherein the filling aperture is disposed on the dispenser so that the bottom wall and filling aperture are opposingly positioned to each other.

17. The device of claim 13, wherein the mounting surface comprises an adhesive.

18. The device of claim 13, wherein the mount comprises a retrieval cutout, and wherein the retrieval cutout is aligned with and positioned proximate to the dispensing aperture when the mount and the dispenser are removably coupled together.

19. The device of claim 13, wherein the second major wall comprises an access aperture that is positioned proximate to the bottom wall.

20. The device of claim 13, wherein the second major wall comprises a viewing aperture, wherein the viewing aperture is located centrally on the second major wall.

* * * * *